United States Patent [19]

Brown

[11] 4,276,284

[45] Jun. 30, 1981

[54] PREVENTION OF COLLAGENASE INDUCED DISEASE BY TREATMENT WITH COLLAGENASE INHIBITORS

[76] Inventor: Stuart I. Brown, 85 East End Ave., New York, N.Y. 10028

[21] Appl. No.: 639,477

[22] Filed: Dec. 10, 1975

Related U.S. Application Data

[63] Continuation of Ser. No. 166,278, Jul. 26, 1971, abandoned, which is a continuation-in-part of Ser. No. 821,505, May 2, 1969, abandoned.

[51] Int. Cl.$^3$ .................... A61K 35/14; A61K 37/00; A61K 31/725; A61K 31/195
[52] U.S. Cl. .................... 424/101; 424/177; 424/183; 424/319; 424/335
[58] Field of Search ............... 424/183, 319, 101, 335, 424/177

[56] References Cited

PUBLICATIONS

*Arch. Ophthal.,* vol. 35, Apr. 1946, pp. 423–449; vol. 52, 1954, pp. 846–851; vol. 54 (1955) pp. 931–939.
*Am. J. Ophthal.* 42 527(1956); vol. 42 part II (1956), pp. 167–181.
*Chemical Abstracts,* vol. 71 (1969), Paragraph 68715h.

*Primary Examiner*—Frederick E. Waddell
*Attorney, Agent, or Firm*—Lawrence E. Laubscher

[57] ABSTRACT

Certain ulcers and disease conditions resulting in tissue destruction, such as those found near the cornea of the eye, and those found in the stomach, and damaged joint tissue of rheumatoid arthritis, have been found to be caused by the enzyme, collagenase. A collagenase inhibitor, such as cysteine, ethylene diamine tetraacetic acid (or sodium ethylene diamine tetraacetate), or combinations of these collagenase inhibitors, are used to treat such ulcers and to inhibit further formation thereof.

6 Claims, No Drawings

PREVENTION OF COLLAGENASE INDUCED DISEASE BY TREATMENT WITH COLLAGENASE INHIBITORS

CROSS-REFERENCE TO RELATED APPLICATION

This application is a continuation of co-pending application Ser. No. 166,278, filed July 26, 1971, which is a continuation-in-part of Ser. No. 821,505 filed May 2, 1969, both now abandoned.

BACKGROUND OF THE INVENTION

The present invention relates to the treatment of ulcers and other disease states evidenced by tissue destruction caused by the enzyme collagenase, and, more especially to the prevention and treatment of the manifested tissue destruction resulting from such disease states.

The prevention and healing of ulcers affecting various parts of the body has long presented difficult problems. For example, in the case of non-infectious ulcers of the cornea and other collagen-based tissue, therapy has generally consisted of simply removing the diseased tissue, typically by surgical operation. It has recently been discovered that a large number of disease states occurring in mammals resulting in ulceration and other destruction of collagen-based tissue cause such damage because they stimulate the production of large amounts of the enzyme collagenase. Brown et al, *Arch. Ophthal.*, vol. 82, July 1969, pp. 95–97; Brown et al, *Arch. Ophthal.*, vol. 83, January 1970, pp. 74–77; Brown et al, *Arch. Ophthal.*, vol. 83, February 1970, pp. 205–208; Brown et al, *Trans. Am. Acad. Ophth. & Otol.*, vol. 74, March–April 1970, pp. 375–582. Based on this discovery, it is now possible to treat the areas of tissue destruction affected by such disease states to inhibit further destruction and thereby promote healing with normal tissue.

SUMMARY OF THE INVENTION

Accordingly, it is a primary object of the present invention to provide a method for the treatment of ulcers and other destruction of collagen-based tissue caused by collagenase-producing disease states.

It is another object of the present invention to provide a method for preventing and treating ulcers associated with alkali-burned corneal tissue and other diseases affecting the cornea.

Another object of the invention resides in the provision of a method for treating ulcers of the gastro-intestinal viscera.

Yet another object of the present invention resides in the provision of a specific therapy for the treatment of tissue destruction occurring in the joint mueosa.

It is a further object of the invention to provide a method for promoting surgical wound healing in tissues where such healing is notoriously poor, i.e., those where collagenalytic enzymes have destroyed tissue.

In attaining the objects of the present invention, one feature resides in a method for preventing damage by the enzyme collagenase to collagen-based cell-lined surface tissues of mammals when such tissue is afflicted with a disease state wherein collagen is broken down by collagenase produced by incoming reparative cells at a greater rate than collagen is produced by incoming fibroblasts. The method comprises direct application to the affected surface tissue of an amount of a collagenase inhibitor effective to reverse the collagen production/destruction balance of the disease state in favor of collagen production. The invention is useful in the treatment of cell-lined surface tissues, either external or internal including the skin and cornea, gastro-intestinal viscera, and joint mucosa.

Other objects, features and advantages of this invention will become more apparent from the description of the invention that follows.

DETAILED DESCRIPTION OF THE INVENTION

Collagen is the major organic component of the surface tissue found in the cornea, skin, gastro-intestinal viscera, joint mucosa and other areas of the body. The collagen molecule has a molecular weight of 300,000, and is composed of three helical polypeptide chains which are wound around a common axis forming a coiled chain. In solution collagen molecules exist as long rods about $3000 \times 15$ Å, but at a temperature of 37° C. and a pH of 7, the molecules polymerize into insoluble fibrils. Thus, it is as fibrils that collagen invariably exists in tissue. The helical structure of undenatured collagen is remarkably resistant to attack by proteolytic enzymes; however, in the last ten years there have been discovered a number of natural enzymes, i.e., animal collagenases, which are capable of breaking down collagen by cleaving the collagen molecule across the helical backbone yielding $\frac{3}{4}$ and $\frac{1}{4}$ length fragments.

While collagenase has been found by others in various diseased mammalian tissues, in no instance has it ever been incriminated as the cause of tissue destruction. In accordance with the discovery underlying the present invention, however, it has been found that the use of collagenase inhibitors in areas of tissue destruction in mammals has produced not only the inhibition of such collagenase, but has also resulted in the successful treatment of the ulcers. The technique is useful in the treatment of all mammals including humans.

The relationship between collagenase and the destruction of collagen-based tissue has been found in a number of disease states affecting various parts of the body, all of which are basically similar in that collagen constitutes the major organic component, e.g., skin, cornea, gastro-intestinal viscera, joint mucosa, etc. For example, in connection with corneal tissue, it has been shown that collagenae is responsible for ulcers appearing after the eye has been burned with alkali. Similarly, the relationship exists for other ulcerous conditions of the cornea such as viral ulcers, e.g., herpes simplex, vaccinia, etc.; bacterial ulcers, e.g., pseudomonas, etc.; degenerative ulcers and ulcers of unknown origin, e.g., associated with rheumatoid arthritis, Mooren's ulcer, furrow ulcer; and ulcers secondary to drying, e.g., erethema multiforme (Stevens-Johnson Syndrome). In addition, the treatment of the invention is useful to promote healing subsequent to corneal transplant surgery.

In this last respect, the invention is broadly applicable to the treatment of surgical wounds and other skin lesions where healing is notoriously poor, e.g., those caused by bed sores and radiation, those related to diabetes, etc.

Other disease states within the contemplation of the present invention include gastric and duodenal ulcers and certain diseases causing destruction of joint tissue, e.g., rheumatoid arthritis, infectious joint diseases of bacterial origin, etc.

The present invention does not reside in the discovery of any particular collagenase inhibitor, but conversely, in the discovery that the manifested tissue destruction associated with various disease states may be treated with an inhibitor for this enzyme. Accordingly, virtually any non-toxic collagenase inhibitor is contemplated within the scope of the instant contribution. A few of the more useful inhibitors presently known include ethylene diamine tetraacetic acid (EDTA), sodium EDTA, calcium EDTA, cysteine, acetyl cysteine, heparin, alpha-2 fraction of the globulin of animal or human serum and British Anti-Lewisite (BAL). Undoubtedly, other useful collagenase inhibitors will be developed based upon the present discovery.

It has been found that certain of the collagenase inhibitors act by different mechanisms to inhibit the enzyme. As a basic premise, it was discovered that collagenase is dependent on calcium for its activity. Thus, the EDTA preparations, which are known powerful chelators, probably inhibit by removal of the essential calcium. Cysteine is known to be a weaker chelator and it has been found that inhibition by this compound occurs through direct attachment to and inactivation of the collagenase molecule. As a result, inhibition by cysteine is irreversible whereas it is not in the case of the EDTA preparations. Thus, from a therapeutic standpoint, the former is clearly more desirable since in the case of a reversible inhibition, its efficacy depends on more frequent administration.

The mode of administration contemplated herein involves direct application of a collagenase inhibitor to the tissue area affected by the destructive condition. Since, in general, this involves topical application of the inhibitor, typically by infusion, and since various inhibitors have different activities as pointed out above, it is not practical to define a dosage level for treatment in accordance with this invention. Typically, the collagenase inhibitors are employed in the form of a dilute aqueous solution, e.g., EDTA 0.01 to 0.1 M, cysteine 0.15 to 0.3 M, acetyl cysteine 0.5 to 1.5 M and alpha-2 fraction of serum globulin 0.1 to 0.5 M. Other pharmacologically acceptable carriers may likewise be employed. Several more specific treatment procedures are discussed immediately below.

In the case of alkali-burned corneal and other detectable disease states of the cornea, it is possible to effectively prevent ulceration in the first instance because of the fact that the disease state can be detected beforehand and treatment can thus begin before tissue damage is manifest. Treatment of the cornea typically involves perfusion of the eye with anywhere from 50 to 200 cc of a dilute aqueous solution of inhibitor from 2 to 10 times daily. Presently preferred is either a 0.15 to 0.3 M solution of cysteine or a combination of same with 0.01 to 0.1 M solution of a sodium salt of EDTA.

Similar treatment procedures are applicable in the case of skin lesions and surgical wounds. One relatively minor difference resides in the choice of other carriers available to produce topical ointments, creams, etc. for application to the skin.

Treatment of gastric and/or duodenal ulcers presents a somewhat different situation from the standpoint of both diagnosis and treatment. Usually, the disease state responsible for the ulcer is not detected or at least appreciated until the ulcer itself appears. Thus, the present invention is most likely of little value as a preventative measure, and generally only proves efficacious for post-detection treatment of the ulcer to prevent further tissue damage and promote healing. Treatment in accordance with the invention cannot, of course, cure the cause of the ulcer, but acts instead to eliminate the destruction of tissue associated with the disease state. In treating the gastro-intestinal viscera, there may be employed a collagenase inhibitor in conjunction with a suitable carrier such as magnesium or aluminum hydroxide, magnesium carbonate hydroxide or tribasic magnesium phosphate. Such preparations are ingested orally. Alternatively, a plastic tube can be inserted through the mouth and led to the site of the ulcer, and through this tube there may be applied to the damaged tissue a solution of inhibitor. Such treatment typically entails washing the stomach with about 100 cc of solution every two hours, to continue along with the usual treatment of such ulcers until healing is established. Presently preferred for such therapy is a 0.15 to 0.35 M aqueous solution of cysteine buffered to a pH of from 4 to 5.

Similar considerations as with gastro-intestinal ulcers are involved with treatment of rheumatoid joints. Again, practically speaking, therapy can be administered only during periods of inflammation, since at other times the disease state is normally not detected. Treatment consists of injecting from 1 to 5 cc of an inhibitor preparation directly into the joint, the amount to depend upon exactly which joint is involved, e.g., about 5 cc for the knee. Injections should continue at the rate of one per day through the acute phases and beyond until the therapist feels the inflammatory response has ended. Generally, periods of from one week to two months are involved. Suitable inhibitor preparations include a 0.15 to 0.3 M solution of cysteine (pH 4–5) and a 0.1 to 0.5 M solution of acetyl cysteine (pH 5–7).

An additional feature of this invention resides in the discovery that treatment of a patient afflicted with one of the above-mentioned disease states with a corticosteroid preparation, e.g., cortisone, cortisol, cortexolone, 11-dehydrocorticosterone, corticosterone, cortexone, etc. results in an increase in the rate of collagenase lysis. Thus, in collegenase producing ulcerous conditions, the use of a corticosteroid for therapy could move the balance in favor of tissue destruction. It is, accordingly, a further advantage of the present invention to counterbalance, by application of a collagenase inhibitor, this enhanced collagenase activity resulting from treatment with a corticosteroid.

By way of theorization, the significance of collagenase production by the healing wound can only be speculated. Since the production seems to parallel the most active fibroblastic and wound healing period, it may be that its physiological role is wound healing is to present collagen precursors to the fibroblasts. Another possibility is that the enzyme acts as a monitor and prevents excessive collagen in the knitting wound. A possible reason that wound collagenase does not cause obvious tissue destruction is that the new collagen produced by the active fibroblast of the normal healing wound more than balances the breakdown by the collagenase.

Not wishing to be bound by this theory, it is possible to speculate on the pathogenesis of ulcers in, for example, the alkali-burned cornea. Alkali applied topically results in immediate death of all the cells of the cornea as well as reduction of the mucopolysaccharide and glycoprotein milieu of the collagen framework. The cornea remains intact and acellular for at least two weeks, whereupon epithelial cells and stromal neovascularization, which is always associated with the repopulation of fibroblasts and polymorphonuclear leukocytes (PMN) begin a slow central progression. Peripheral to the advancing border of new cells, collagenase is produced, primarily in the stroma, by the PMN and possibly the fibroblasts. The cornea remains intact peripheral to the advancing border of the new cells because collagen destruction by collagenase is counterbalanced by the collagen production of the many incoming fibroblasts. However, at the periphery of the advancing border of cells, the area where ulcers invariably occur, there are few fibroblasts. In this area, the epithelium is stimulated to produce large amounts of enzyme which, coupled with that produced by the PMN, causes destruction.

The discoveries leading to the invention may explain why slow wound healing and stromal melting on the host side of the wounded areas are noted when grafts are used on alkali-burned corneas. Collagenase probably is being produced in the host stroma, but its activity is balanced by collagen production. Characteristically, the epithelium is slow to bridge the wound, and consequently there is a prolonged production of additional collagenase by the marginal epithelium under the influence of the wound fibroblasts. This increased enzyme production alters the balance, and collagen destruction occurs.

The following examples will serve to illustrate the invention, it being understood that the same are merely intended to be illustrative and in no wise limitative.

EXAMPLE 1

Polyethylene tubes were implanted into adult albino rabbits in order to be certain of the quantity of drugs delivered to the corneas of the rabbits. The technique of Hessburg et al ("Corneal Infections in Experimental Animals", American Journal Ophthalmology, vol. 53, page 359, 1962) was somewhat modified. After intravenous pentabarbital, subcutaneous procaine, and topical tetracaine anesthesias, the tubes were implanted by passing a trocar up from the conjunctival fornix to extend under the skin and exit between the ears of the rabbits. The polyethylene tube was advanced through the trocar which was removed, leaving the polyethylene tube in place. The conjunctival end of the tube was flared with heat and this end was pulled to the upper extremity of the superior fornix. A second tube with flared end down was placed over the exposed portion of the first tube which was also flared. The composite tube was designed to prevent downward excursions which could erode the cornea.

Twenty-four hours after implantation, a cotton pledget soaked with 0.5 N sodium hydroxide was applied for thirty seconds to the corneas and surrounding sclerras of the rabits' eyes. Twenty-four to thirty-six hours after exposure to the alkali, the animals were placed in restraining cages and nineteen gauge blunt needles were inserted into the exposed portions of their implanted polyethylene tubes and their corneas were profused twice daily with the following:

A. 100 cc of rabbit serum 10% dilution with 0.9% sodium chloride—4 eyes.

B. 50 cc of cysteine 0.10 M followed by 50 cc disodium EDTA 0.1 M—8 eyes.

C. 100 C of 0.9% sodium chloride—4 eyes.

Between the third and fourth week after exposure to the alkali, corneal ulcers were noted in all of the eyes profused with either the rabbit serum or the 0.9% sodium chloride. These corneas perforated by the end of the fourth week. However, only one of the corneas that was profused with cysteine and EDTA perforated after six weeks.

After eight weeks, a small, but deep ulcer was noted in the superior periphery of one of the corneas treated with the EDTA—cysteine mixture, and this ulcer was located directly below the profusion tube orifice. All of the saline and serum treated corneas had varying degrees of neovascularization prior to perforation. However, no vascularization was noted in the EDTA—cysteine treated corneas.

The results of the example show that profusion of alkali-burned corneas with cysteine and EDTA prevented the ulcers and perforations of the alkali-burned corneas for ten weeks in six of the eight eyes treated. In one of the other two eyes, perfusion delayed the appearance of ulcers until the eighth week. After ten weeks, one of these two eyes had still not perforated. Perfusion with rabbit serum proved to be ineffectual since all the serum-treated corneas perforated during the fourth week, as did the controls. A comparison of the EDTA—cysteine treated animal with the controls leaves no doubt that collagenase is involved in the production of the ulcers of the alkali-burned cornea, and that the use of collagenase inhibitors inhibits the formation of such ulcers.

EXAMPLE 2

A patient having a chemical burn of the cornea for a period of two years was accepted for treatment. The burn resulted in an opaque cornea and conjunctival overgrowth. Treatment consisted of a conjunctival resection and a corneal graft. Postoperatively, the graft was clear, but the epithelium did not bridge the wound along much of the circumference. The epithelium remained at the wound edge for nine weeks, at which time it was observed that the host side of the wound had begun to melt. The patient was treated by perfusing 100 cc of a 0.2 M solution of cysteine in 0.9% sodium chloride six times daily. Within one day the epithelium bridged the wound, four days later the graft was completely covered by epithelium and stromal melting had stopped. Six months postoperatively the graft was transparent, and the patient's visual acuity was 20/40 with a contact lens.

EXAMPLE 3

A 26-year old male patient had an alkali preparation thrown into both eyes. This resulted in burns of both corneas, the surrounding sclera, and the conjunctiva of both inferior fornices. The most severely burned eye was topically treated with irrigations of 1 cc of 0.15 M cysteine four times a day, while the other eye received only antibiotics. The eye not treated with the collagenase inhibitor perforated three weeks after exposure to the alkali, whereas the treated eye remained intact.

EXAMPLE 4

A patient suffering from a gastric ulcer is treated in the following manner: a Levine tube is passed orally into the stomach and the gastric juices are removed. The juices are replaced with 100 cc of a 0.4 M solution of acetyl cysteine in a 0.9% NaCl having a pH of 5. This procedure is repeated at intervals of every two hours in conjunction with conventional treatment practices. X-ray examination reveals excellent response to treatment with complete healing within several weeks.

EXAMPLE 5

A patient having an inflamed rheumatoid knee joint is given an injection of 4 cc of a 0.2 M solution in cysteine in 0.9% NaCl (pH 4) directly into the synovial fluid of the joint. This treatment is continued once daily for a period of 4 weeks, after which period the acute phase has subsided and the inflammatory response has ended.

While the invention has been described and pointed out with reference to certain preferred embodiments thereof, those skilled in the art will appreciate that various changes, modifications, substitutions and omissions can be made by those skilled in the art without departing from the spirit of the invention. It is intended, therefore, that the invention be limited only by the scope of the claims which follow.

What is claimed is:

1. A method for preventing ulceration of corneal tissues when said tissue is afflicted with an ulcerous condition consisting of Stevens-Johnson Syndrome wherein collagen is broken down by collagenase produced by incoming reparative cells at a greater rate than collagen is produced by incoming fibroblasts, which method comprises the steps of applying to the afflicted tissue an amount of a non-toxic collagenase inhibitor effective to reverse the collagen production/destructon balance of said disease state in favor of collagen production and periodically repeating said application step to maintain the collagen production/destruction balance in favor of collagen production until said ulcerous condition is eliminated.

2. A method for preventing ulceration of corneal tissues when said tissue is afflicted with an ulcerous condition comprising normal healing post-operative to a corneal transplant operation wherein collagen is broken down by collagenase produced by incoming reparative cells at a greater rate than collagen is produced by incoming fibroblasts, which method comprises the steps of applying to said tissue an amount of a non-toxic collagenase inhibitor effective to reverse the collagen production/destruction balance of said disease state in favor of collagen production and periodically repeating said application step to maintain the collagen production/destruction balance in favor of collagen production until said ulcerous condition is eliminated.

3. A method for preventing ulceration of gastro-intestinal viscera tissue when said tissue is afflicted with an ulcerous condition wherein collagen is broken down by collagenase produced by incoming reparative cells at a greater rate than collagen is produced by incoming fibroblasts, which method comprises the steps of applying to the afflicted tissue an amount of a non-toxic collagenase inhibitor effective to reverse the collagen production/destruction balance of said disease state in favor of collagen production and periodically repeating said application step to maintain the collagen production/destruction balance in favor of collagen production until said ulcerous condition is eliminated.

4. The method of claim 3, wherein said application step comprises orally ingesting a composition comprising collagenase inhibitor in combination with a pharmaceutically acceptable carrier.

5. The method of claim 4, wherein said composition is orally ingested every 2 hours until healing of the ulcerous condition is achieved.

6. A method for preventing ulceration of joint mucosa tissues when said tissue is afflicted with an ulcerous condition wherein collagen is broken down by collagenase produced by incoming reparative cells at a greater rate than collagen is produced by incoming fibroblasts, which method comprises the steps of directly injecting into the affected joint from about 1 to 5 cc of a composition comprising a collagenase inhibitor in combination with a pharmaceutically acceptable carrier effective to reverse the collagen production/destruction balance of said disease state in favor of collagen production and periodically repeating said injection step to maintain the collagen production/destruction balance in favor of collagen production until said ulcerous condition is eliminated.

* * * * *

UNITED STATES PATENT AND TRADEMARK OFFICE
CERTIFICATE OF CORRECTION

PATENT NO. : 4,276,284

DATED : June 30, 1981

INVENTOR(S) : Stuart I. Brown

It is certified that error appears in the above—identified patent and that said Letters Patent is hereby corrected as shown below:

On the Title page insert Item [73] Assignee:

Cornell Research Foundation, Inc.

Ithaca, New York

Signed and Sealed this

Fifteenth Day of June 1982

[SEAL]

*Attest:*

*Attesting Officer*

GERALD J. MOSSINGHOFF

*Commissioner of Patents and Trademarks*